United States Patent [19]
Funakoshi et al.

[11] 4,137,307
[45] Jan. 30, 1979

[54] PROCESS FOR PREPARING HAPTOGLOBIN AQUEOUS SOLUTION USING STRONG ANION EXCHANGER

[75] Inventors: Satoshi Funakoshi, Katano; Takao Omura, Toyonaka; Takeshi Ohshiro, Osaka, all of Japan

[73] Assignee: The Green Cross Corporation, Osaka, Japan

[21] Appl. No.: 788,921

[22] Filed: Apr. 19, 1977

Related U.S. Application Data

[60] Division of Ser. No. 677,085, Apr. 15, 1976, Pat. No. 4,061,735, and a continuation-in-part of Ser. No. 444,662, Feb. 21, 1974, abandoned.

[30] Foreign Application Priority Data

Nov. 15, 1973 [JP] Japan .................................. 48-128605
Nov. 15, 1973 [JP] Japan .................................. 48-128606

[51] Int. Cl.² ...................... A61K 37/04; A61K 37/06; C07G 7/00
[52] U.S. Cl. ................................. 424/177; 260/112 B
[58] Field of Search ...................... 424/177; 260/112 B

[56] References Cited
PUBLICATIONS

Betlach et al. — Chem. Abst., vol. 77, (1972), p. 85167x.
Oh et al. — Chem. Abst., vol. 76, (1972), p. 82426z.
Betlach et al. — Annals of Biochemistry, vol. 49, No. 1, (1972), pp. 103-108.

*Primary Examiner*—Sam Rosen
*Attorney, Agent, or Firm*—Cushman, Darby & Cushman

[57] ABSTRACT

An aqueous solution of haptoglobin is obtained by subjecting an aqueous solution of α and β-globulin fractions of human blood plasma to further fractionation by use of ammonium sulfate, collecting fractions precipitated at a concentration between 30% and 40% saturation of ammonium sulfate, contacting a reconstituted aqueous solution of the collected fractions with an anion exchanger to adsorb haptoglobin on said anion exchanger, selectively eluting the haptoglobin from the anion exchanger, and then concentrating the resulting aqueous eluate solution. The aqueous solution of haptoglobin is subjected to heat treatment in the presence of a selected stabilizing agent for inactivating hepatitis B virus at an optional step of the process.

The thus obtained aqueous solution of haptoglobin has less than 10% hypotensive activity, highly stable during storage, and free from the risk of hepatitis B virus infection. This haptoglobin preparation is used for prevention and treatment of renal disorders caused by hemolysis.

17 Claims, 1 Drawing Figure

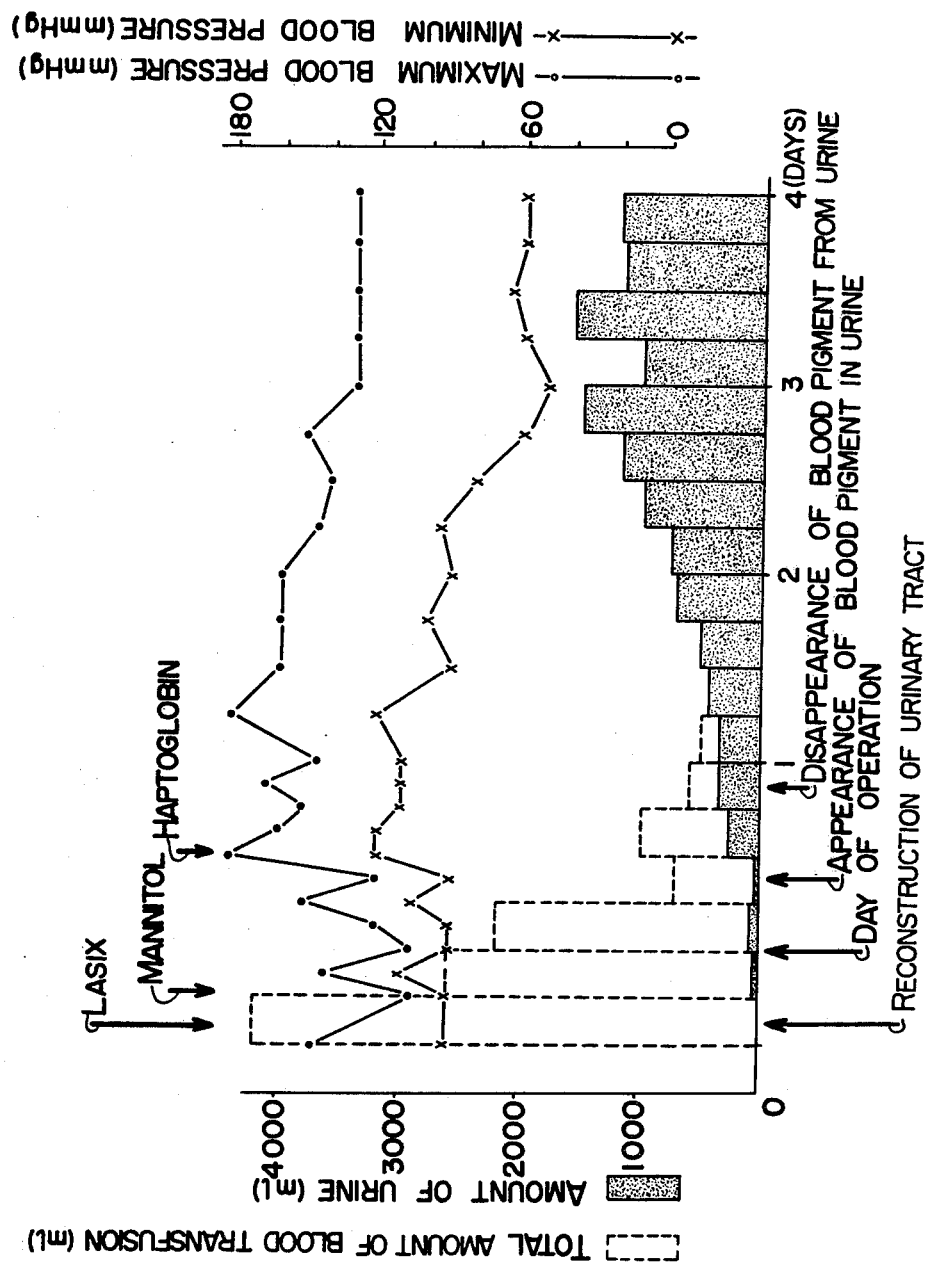

PROCESS FOR PREPARING HAPTOGLOBIN AQUEOUS SOLUTION USING STRONG ANION EXCHANGER

CROSS REFERENCE TO THE RELATED APPLICATION

This is a division of application Ser. No. 677,085 filed Apr. 15, 1976 and now U.S. Pat. No. 4,061,735 and is a continuation-in-part of application Ser. No. 444,662 filed Feb. 21, 1974 and now abandoned.

This invention relates to an aqueous solution of human serum haptoglobin and to a process for preparing the same. More particularly, the invention pertains to a haptoglobin preparation capable of being administered in a large amount for the therapy of renal disorders derived from excessive hemolysis, and to a process for producing the said preparation.

Haptoglobin is a protein having a molecular weight of 85,000 to 400,000 and plays an important role in the metabolism of hemoglobin liberated in the blood. When massive hemolysis occurs, plasma haptoglobin is soon consumed and the excess free hemoglobin whose molecular weight is about 67,000 is transported to the kidney and excreted into urine through glomeruli, whereby not only the blood iron is consumed but also troubles of tubuli (tubuli renales) are brought about.

Haptoglobin binds selectively and firmly to hemoglobin to form a haptoglobin-hemoglobin complex, which is easily accepted chiefly by parenchymal cells of the kidney and is metabolized therein to provide such important functions as the recovery of iron and the prevention of renal disorders.

Severe hemolysis, i.e. liberated free hemoglobin, is usually accompanied by renal disorders which often leads to uremia and is fatal to the host. At present, therefore, hemolytic renal disorders derived from heterotypic blood transfusions, heavy burns, cardiac operations, hemolytic diseases, etc. are serious problems. While symptomatic treatment for said troubles has been proposed hitherto, such a causal treatment as to normalize the metabolism and excretion of hemoglobin which results from bonding haptoglobin to hemoglobin, like the drug prepared according to the present invention, has first been proposed by the present inventors.

The accompanying drawing shows the clinical progress of a patient by treatment with a haptoglobin preparation obtained according to the process of the present invention.

An object of the present invention is to provide an aqueous solution of human serum haptoglobin.

Another object of the invention is to provide a highly purified human serum haptoglobin containing practically no hypotensive substances.

A further object of the invention is to provide an aqueous solution of a purified haptoglobin subjected to a treatment inactivating hepatitis B virus (hereinafter referred to as HB-Ag).

A still other object of the invention is to provide a process for preparing the above-mentioned aqueous solution of human serum haptoglobin.

A further object of the invention is to provide a process of treatment for inactivating HB-Ag suspected in an aqueous solution of human serum haptoglobin.

Other objects and advantages of the invention will become apparent from the description given below.

The accompanied drawing shows the clinical progress, after administration of the haptoglobin preparation prepared according to the present invention, of a patient suffering from pelvis fracture, urethra rupture and bleeding shock.

In order to bring free hemoglobin, which has been liberated in the blood stream due to various types of hemolysis, to the form of a haptoglobin-hemoglobin complex and to prevent or treat renal disorders, a large amount of haptoglobin is required to be administered. It is therefore desirable that the haptoglobin has been highly purified. Further, fractions of human blood plasma not only contain hypotensive substances but also cannot always be free from contamination with HB-Ag. Even if the fractions are HB-Ag negative as the result of its examination, it is not always possible that there is no risk of infection. Accordingly, the removal of said hypotensive substances and the inactivation of said HB-Ag are important in those cases where the said fractions are desired to be used as medicaments.

The aqueous solution of haptoglobin prepared according to the present invention not only satisfies the above-mentioned conditions but also can be produced in large quantities on a commercial scale.

The aqueous solution of haptoglobin provided by the present invention is obtained by subjecting an aqueous solution of $\alpha$- and $\beta$-globulin fractions of human blood plasma to further fractionation by use of ammonium sulfate, collecting fractions precipitated at a concentration between 30% and 40% saturation of ammonium sulfate, contacting the reconstituted aqueous solution of the collected fractions with an anion exchanger to adsorb haptoglobin onto the anion exchanger, selectively eluting the haptoglobin from the anion exchanger, and then concentrating the resulting aqueous eluate.

The preparation procedure of the present invention is extremely economical and advantageous; first, $\alpha$- and $\beta$-globulin fractions which are byproducts obtained in the process of fractionation of major plasma proteins such as fibrinogen, $\gamma$-globulin, albumin, etc. that are ordinarily used for the production of important biological drugs may be used as the starting material, and second, the preparation process can be conducted at room temperature. The $\alpha$- and $\beta$-globulin fractions used in the present invention correspond to, for example, the fractions IV, IV-1 and IV-4 according to Cohn's low temperature alcohol fractionation method (Cohn E. J., Strong L. E., Hughes W. L., Mulford D. J., Ashworth J. N., Melin M. and Taylor H. L.: Journal of the American Chemical Society, 68 459, 1946). According to a method other than the Cohn's fractionation method, e.g. an ammonium sulfate precipitation method, substantially the same $\alpha$- and $\beta$-globulin fractions as those mentioned above can also be obtained as fractions precipitated at a concentration between 35 to 50% saturation of ammonium sulfate. These fractions may also be used as starting materials in the present invention.

The above-mentioned $\alpha$- and $\beta$-globulin fractions are dissolved in 3 to 10 times the volume thereof of a buffer solution having a pH of 6 to 9, preferably about 8, to form an aqueous solution which is turbid in most cases. This aqueous solution, either as is or after clarification by centrifugal separation, is freed from residual ethanol by dialysing it against buffer solution (pH 6-9).

An aqueous solution of rivanol is added to this solution so that the concentration of rivanol becomes 0.2 to 0.6%, preferably 0.4%, by weight based on the volume of the solution, whereby precipitates are formed. The precipitates are removed by filtration or centrifugal separation, and rivanol remaining in the aqueous solution is removed by, for example, dialysis against buffer solution, or adsorption on bentonite, terra alba or active carbon as an adsorbent. The said rivanol treatment is important for clarification of the aqueous solution in order to make the progress of subsequent processes smooth.

The thus clarified aqueous solution is adjusted to a pH of 5.5 to 8.0, preferably 7.0. An aqueous concentrated ammonium sulfate solution is added to said aqueous solution, and precipitates formed at the concentration of 30% w/v saturation of ammonium sulfate are removed. The said ammonium sulfate solution is further added to the supernatant, and precipitates formed at a concentration of 40% w/v saturation of ammonium sulfate are collected. In the above manner, fractions precipitated at a concentration between 30% w/v and 40% w/v saturation of ammonium sulfate are collected, in general. The symbol "% w/v" means "% by weight based on the volume of the solution".

According to the fractionation by ammonium sulfate, transferrin, albumin and other undesirable proteins in the α- and β-globulin fractions are removed.

The aforesaid clarification method of the aqueous solution of the α- and β-globulin fractions with rivanol is applicable also to the reconstituted solution of said ammonium sulfate-precipitates. The fractions precipitated by ammonium sulfate are dissolved in 3 to 10 times the volume thereof of an acetate buffer solution having a pH of 4.5 to 8.5, preferably 5.5, and an ionic strength of 0.01 to 0.08, e.g. a 0.05M, and the resulting solution is brought into contact with a strong anion exchanger equilibrated with the same buffer solution as above, preferably QAE-Sephadex [tradename of epichlorohydrin-crosslinked diethyl(2-hydroxypropyl)aminoethyl-dextran supplied by Pharmacia Co.] or guanidoethyl cellulose. The anion exchanger which has adsorbed haptoglobin is washed, if necessary, with a small amount of the aforesaid buffer solution having a low ionic strength, and then eluted with a buffer solution having an ionic strength of 0.25 to 0.35 and a pH of 4.5 to 8.5, preferably 5.5, e.g. a 0.05M acetate buffer solution adjusted to the above-mentioned ionic strength by addition of sodium chloride, to obtain an aqueous haptoglobin eluate.

By this step, the greater portion of the hypotensive substances and of unstable substances causing turbidity or precipitation during storage contained in the aqueous solution are separated from haptoglobin.

The thus obtained eluate containing haptoglobin is then concentrated according to, for example, an ammonium sulfate precipitation method carried out by precipitating all the proteins present in the solution, and dissolving the precipitates in a proper amount of a suitable solvent, preferably a physiologically acceptable aqueous solution, e.g. an isotonic sodium chloride solution. Alternatively, the aqueous solution may be concentrated by dialysis under reduced pressure. When the dialysis under reduced pressure is conducted against physiologically acceptable aqueous solution, the eluate containing haptoglobin can be formed at one stage into a physiologically acceptable solution.

The aqueous solution of haptoglobin obtained according to the present invention can be freely controlled in its haptoglobin concentration by varying the degree of concentration of the solution. In case the aqueous solution is desired to be used as an intravenous injection for the prevention or treatment of renal disorders derived from free hemoglobin caused by massive hemolysis, however, the haptoglobin concentration thereof is preferably concentrated to the range of from 5 to 15% by weight based on the volume of the solution. The purity of the haptoglobin of this aqueous solution is at least 65% and the yield thereof is at least 30%. Further, the amounts of hypotensive substances and unstable substances in said aqueous solution are far smaller than in the aqueous solution before the treatment with the anion exchanger. It is needless to say that the aqueous solution is subjected to sterile filtration or the like to give an aseptic drug for clinical application.

Haptoglobin in the form of an aqueous solution is not sufficiently stable to heat, and substantially loses its activity when subjected to a heat treatment for the inactivation of HB-Ag which is employed in the production of an albumin preparation. According to the experiments carried out by the present inventors, the activity of haptoglobin in an aqueous solution always becomes substantially nil when subjected to heat treatment at 60° C. for 10 hours which is generally known as an HB-Ag inactivation treatment.

The present inventors have found that when an aqueous solution of haptoglobin was added with a certain stabilizing agent, the haptoglobin becomes stable to heat. That is, an aqueous solution of haptoglobin added with a stabilizer such as neutral amino acid, monosaccharide, disaccharide or sugar alcohol is stable to heat, and does not lose its activity even when subjected to a heat treatment at 60° C. for 10 hours which is required for inactivation of HB-Ag. The above-mentioned stabilizers may be used either singly or in combinations of two or more of such agents.

The above-mentioned heat stabilization procedure may be applied to the aqueous solution at any step during the process for preparation of the final haptoglobin solution. That is, any of the starting aqueous solution of α- and β-globulin fractions, the rivanol-clarified aqueous solution, the rivanol-free aqueous solution, the aqueous reconstituted solution of ammonium sulfate precipitates, the aqueous eluate formed by elution from the anion exchanger, and the concentrated aqueous solution may be added with the above mentioned stabilizer and then subjected to heat treatment for inactivation of HB-Ag.

Concrete examples of the stabilizer are neutral amino acids (monoamino-monocarboxylic acids) such as glycine, alanine, valine, leucine and isoleucine, monosaccharides such as glucose, mannose, galactose and fructose, disaccharides such as sucrose, maltose and lactose, and sugar alcohols such as mannitol, sorbitol and xylitol. The amount of stabilizer to be used is at least 5%, preferably 15 to 20%, by weight based on the volume of the solution.

The heat treatment to inactivate HB-Ag is effected according to a conventional procedure. When treated under such conventional conditions as 60° C. and 10 hours, the aqueous solution still maintains a haptoglobin activity of 95%.

The stabilizer remaining in the aqueous solution used for inactivating HB-Ag is removed by dialysis, or may be removed by dialysis under reduced pressure or the ammonium sulfate precipitation treatment adopted in the step of concentrating the aqueous solution.

The procedure for stabilizing haptoglobin in an aqueous solution of the present invention may be applied also to an aqueous solution of haptoglobin obtained according to other experimental processes; one of which is proposed by Betrach and McMillan [Anal. Biochem., 49, 103–108 (1972)].

The toxicity of the aqueous solution of haptoglobin provided by the present invention is extremely low, and brings about no adverse effects even when injected in large quantities not only into the mouse or rat but also into humans. For example, even when the aqueous solution of haptoglobin in the form of a 5% solution of haptoglobin in isotonic sodium chloride is given dropwise intravenously into a human adult, no adverse effect is observed at all.

The present invention is illustrated in detail below with reference to the examples, but the examples do not limit the scope of the invention.

In the examples, the hemoglobin-binding capacity of haptoglobin is represented by the amount of the maximum addition of hemoglobin at which no free hemoglobin was observed in a test system where an optional amount of hemoglobin was added to a definite amount of haptoglobin, and the resulting mixture was developed according to the method of polyacrylamide gel thin layer electrophoresis followed by staining with a benzidine reagent (The Society of the Electrophoresis: Experimental Methods by Electrophoresis, page 247, published by Bunkodo).

The total amount of haptoglobin was measured according to the single radial immunodiffusion method proposed by Mancini G, Carbonara A. O. and Heremans J. F.: Immunochem., 2, 235 (1965) using rabbit anti-haptoglobin sera prepared by the inventors and served by Behringwerke Co. The purity of haptoglobin was represented by the percentage of haptoglobin to the amount of total protein of the preparation which was calculated by measuring the nitrogen content according to the Kjeldahl method and by multiplying the said contents by 6.25.

The acute toxicity was represented by $LD_{50}$ measured when the aqueous haptoglobin solution was intravenously injected into mice and rats. The hypotensive activity was represented by the ratio of arterial blood pressure of the dog before and after administration of haptoglobin solution. A ratio less than 10% was evaluated as hypotensive activity negative. The measurement of HB-Ag was made by the radioimmunoassay method (Sadatake Kato et al.: Japanese Patent Publication No. 49,919/73) using Ausria-125 kit, products of Abbott Co.

EXAMPLE 1

Thirty kilograms of fraction IV obtained by fractionating human blood plasma according to Cohn's low temperature ethanol fraction method were suspended in 145 liters of a pH of 8.2, 0.05M ammonium acetate buffer solution. The resulting suspension was mixed with 120 liters of a 1% aqueous rivanol solution, stirred for 3 hours and then allowed to stand for 2 hours to deposit precipitates. The precipitates were removed by centrifugal separation, and the supernatant was mixed with 8 kg of bentonite, stirred for 2 hours and then filtered to obtain a clear solution. After adjusting the pH of the filtrate to 7.0 by addition of 1N acetic acid, ammonium sulfate was added thereto to give a final concentration of 30% the saturation, and the precipitates formed were removed by centrifugation. Thereafter, ammonium sulfate was further added to give a concentration of 40% the saturation, and the precipitates formed were recovered by centrifugation. The recovered precipitates were dissolved in 10 liters of a 0.05M sodium acetate solution and dialyzed against the same buffer solution. The resulting solution was added with glycine so as to give a glycine concentration of 20% (W/V), the pH was adjusted to 8 and then the solution heated in a thermostat equipped water bath at 60° C. for 10 hours. The heat-treated solution was dialyzed against 0.05M acetate buffer solution (pH 5.0) and then mixed with 200 g of QAE-Sephadex A-50, which was previously equilibrated with the same buffer solution as that mentioned above, to adsorb haptoglobin thereon. The QAE-Sephadex A-50, which adsorbed the haptoglobin, was washed with a buffer solution having an ionic strength of 0.05 (composition: 0.05M $CH_3COOH$ + 0.05M $CH_3COONa.3H_2O$) and then with a buffer solution having an ionic strength of 0.3 (composition: 0.05 M $CH_3COOH$, 0.05M $CH_3COONa.3H_2O$ + NaCl) to elute the haptoglobin therefrom. Ammonium sulfate was added to the eluate to give a concentration of 50% of saturation, and the precipitates formed were recovered by filtration and dissolved in 1.5 liters of an isotonic sodium chloride solution. The resulting solution was dialyzed and then passed through a 0.2 micron-millipore filter membrane to obtain a sterile aqueous solution of haptoglobin. The haptoglobin concentration of this aqueous solution was 4.8%, and the yield of haptoglobin was 42%. The properties of the haptoglobin are shown in Table 1.

Table 1

| Measured items | Results |
| --- | --- |
| Haptoglobin purity | 75% |
| Hemoglobin-binding capacity | 0.62 mg hemoglobin/mg haptoglobin |
| $LD_{50}$   Mice | 11.7 g/kg or more |
| Rats | 10.5 g/kg or more |
| Hypotensive activity | 9.5% |
| HB-Ag | Negative |

In order to show the effect of the treatment with an ion exchanger, the results of comparison in hypotensive activity and stability through storage between the haptoglobin solutions before and after the treatment are set forth in Table 2.

Table 2

| | Hypotensive activity (%) | Stability | |
| --- | --- | --- | --- |
| | | Stored at 4° C for 3 months | Stored at room temp. for 3 months |
| Before treatment | 18 | Fine substances suspended | Fine substances suspended |
| After treatment | 9.5 | Unchanged, clear | Unchanged, clear |

EXAMPLE 2

Three kilograms of fraction IV obtained by fractionating human blood plasma according to Cohn's ethanol fractionation method were suspended in 15 liters of an acetate buffer solution having a pH of 7. The resulting suspension was dialyzed against acetate buffer solution and then centrifuged to removed ethanol and insolubles, respectively. To the supernatant, ammonium sulfate was added to give a concentration of 33% of saturation, and the precipitates formed were removed by centrifugation. Thereafter, ammonium sulfate was further added to give a concentration of 40% of saturation, and the precipitates formed in this case were recovered by filtration. The recovered precipitates was dissolved in 10 liters of water, and the resulting solution was mixed with 8 liters of 0.5% rivanol solution and adjusted to pH to 7.5. Subsequently, the solution was centrifuged to remove precipitates, and the supernatant was dialyzed against acetate buffer solution to remove rivanol. The dialyzed solution was mixed with 20% by weight based on the volume thereof of mannitol and then heated at 60° C. for 10 hours. The heat-treated solution was dialyzed against 0.05M acetate buffer solution (pH 6.5) to remove mannitol, whereby 1.2 liters of a 3% aqueous haptoglobin solution was obtained. The thus obtained haptoglobin solution was mixed with 30 g of GE Cellulose (guanidoethyl cellulose, product of Serva Co.), which was previously equilibrated with the same buffer solution as above, to adsorb haptoglobin on said GE Cellulose. The GE Cellulose adsorbed haptoglobin was washed with an aqueous solution having an ionic strength of 0.08 (composition: 0.08M $CH_3COOH$ + 0.08M $CH_3COONa.3H_2O$) and then with an aqueous solution having an ionic strength of 0.25 (composition: 0.08M $CH_3COOH$ + 0.08M $CH_3COONa.3H_2O$ + NaCl) to elute the haptoglobin therefrom. The eluates were collected, dialyzed under reduced pressure against isotonic sodium chloride solution, concentrated and then passed through a 0.2 micron millipore filter membrane to obtain a sterile aqueous haptoglobin solution. The protein concentration of this solution was 10% and the yield of haptoglobin was 40%. The properties of the haptoglobin are shown in Table 3.

Further, in order to show the effect of the treatment with the ion exchanger, the results of comparison in hypotensive activity and aging effect between the haptoglobin solutions before and after the treatment are set forth in Table 4.

Table 3

| Measured items | Results |
| --- | --- |
| Haptoglobin purity | 71% |
| Hemoglobin-binding capacity | 0.68 mg hemoglobin/mg haptoglobin |
| $LD_{50}$  Mice | 12 g/kg or more |
| Rats | 10 g/kg or more |
| Hypotensive activity | 6.0% |
| HB-Ag | Negative |

Table 4

| | Hypotensive activity (%) | Aging effect | |
| --- | --- | --- | --- |
| | | Stored at 4° C for 3 months | Stored at room temp. for 3 months |
| Before treatment | 12.0 | Fine precipitates | Slightly turbid |
| After treatment | 6.0 | Unchanged, clear | Unchanged, clear |

EXAMPLE 3

Ten liters of a pool of fresh blood plasma were subjected to the ammonium sulfate precipitation method to obtain α- and β-globulin fractions. This was added to 10 liters of an ammonium acetate buffer solution at pH 8 to make suspension. The resulting suspension was mixed with 7 liters of a 1% aqueous rivanol solution and allowed to stand for 2 hours. The precipitates formed were removed by centrifugation, and the supernatant was mixed with 0.6 kg of terra alba, stirred for 2 hours and then filtered to obtain a clear solution. After adjusting the pH of the filtrate to 7.0 by addition of 1N acetic acid, ammonium sulfate was added to give a concentration of 30% of saturation, and the precipitates formed were removed by centrifugation. To the supernatant, ammonium sulfate was further added to give a concentration of 40% of saturation, and the precipitates formed in this case were collected by centrifugation. The collected precipitates were dissolved in water, and the resulting solution was dialyzed against 0.05M acetate buffer solution at pH 5.5. The dialysate was subjected to chromatography using a 4 cm × 30 cm column packed with QAE-Sephadex A-50. Subsequently, the column was washed with acetate buffer solution of ionic strength of 0.12 and then with acetate buffer solution having an ionic strength of 0.3 to elute haptoglobin. The eluted haptoglobin was concentrated with the aid of polyethylene glycol as a water-absorbing agent, and the concentrated liquid was mixed with 15% by weight, based on the volume thereof, of glycine and then heated at 60° C. for 10 hours. The heat-treated liquid was dialyzed against isotonic sodium chloride solution to remove the glycine and then passed through a 0.2 micron-millipore filter membrane to obtain a sterile isotonic sodium chloride solution of haptoglobin. The protein concentration of this solution was 8.2% and the yield of haptoglobin was 38%. The properties of the haptoglobin are shown in Table 5.

Further, in order to show the effect of the treatment with the ion exchanger, the results of comparison in hypotensive activity and aging effect between the haptoglobin solutions before and after the treatment are set forth in Table 6.

Table 5

| Measured items | Results |
| --- | --- |
| Haptoglobin purity | 91% |
| Hemoglobin-binding capacity | 0.88 mg hemoglobin/mg haptoglobin |
| $LD_{50}$  Mice | 12 g/kg or more |
| Rats | 10 g/kg or more |
| Hypotensive activity | 7.0% |
| HB-Ag | Negative |

Table 6

| | Hypotensive activity (%) | Aging effect | |
| --- | --- | --- | --- |
| | | Stored at 4° C for 3 months | Stored at room temp. for 3 months |
| Before treatment | 24.0 | Fine precipitates | Slightly turbid |
| After treatment | 7.0 | Unchanged, clear | Unchanged, clear |

EXAMPLE 4

When the heat treatment for inactivating HB-Ag suspected in a haptoglobin solution is carried out in the absence of stabilizer, the haptoglobin lost its hemoglobin-binding capacity.

In this example, the relation between the amount used and the stabilizing effects of various stabilizers was examined by measuring the residual hemoglobin-binding capacity of haptoglobin after heat treatment.

The haptoglobin solution used in this experiment was the isotonic sodium chloride solution before heat treatment obtained in Example 1. The stabilizers used were glycine and alanine as neutral amino acids, and mannitol and glucose as saccharides. Each of the said stabilizers was dissolved in haptoglobin solution in such proportions as shown in Table 7 and then heated at 60° C. for 10 hours. Thereafter, the hemoglobin-binding capacity of the haptoglobin of the solution was measured, and the ratio thereof to the value before heat treatment represented by percentage.

For comparison, the haptoglobin solution without addition of stabilizer was subjected to the same heat treatment as above, and the hemoglobin-binding capacity of haptoglobin of the solution was measured.

The results obtained are shown in Table 7.

Table 7

| Stabilizer | | Residual hemoglobin-binding capacity of haptoglobin after heat treatment (%) |
|---|---|---|
| Kind | Amount (%) | |
| Glycine | 20 | 95 |
| | 15 | 95 |
| | 10 | 70 |
| | 5 | 35 |
| | 2.25 | 20 |
| Alanine | 20 | 75 |
| | 15 | 50 |
| | 20 | 85 |
| | 15 | 80 |
| Mannitol | 10 | 55 |
| | 7 | 40 |
| | 5 | 15 |
| Glucose | 20 | 60 |
| | 15 | 45 |
| None | | ≈ 0 |

EXAMPLE 5

Example 4 was repeated except that the haptoglobin solution was replaced by the dialysate before heat treatment obtained in Example 3 and sorbitol and sucrose were additionally used as the stabilizers.

The results obtained are shown in Table 8.

Table 8

| Stabilizer | | Residual hemoglobin-binding capacity of haptoglobin after heat treatment (%) |
|---|---|---|
| Kind | Amount (%) | |
| Glycine | 20 | 92 |
| Alanine | 20 | 83 |
| Mannitol | 20 | 85 |
| Glucose | 20 | 72 |
| Sorbitol | 20 | 76 |
| Sucrose | 20 | 68 |
| None | | 0 |

EXAMPLE 6

The haptoglobin solution prepared in Example 1 was subjected to in vivo experiments in rabbits to see the effect of haptoglobin treatment after hemoglobin administration.

Thirty mature rabbits of body weight ranging from 2.3 to 2.9 kg were equally divided into 3 groups (10 rabbits per group), and continuously administered with haptoglobin and/or hemoglobin, and then the survival of the rabbits was observed. At the end of the observation, the survived rabbits were anatomized, and various organs thereof were subjected to histopathological examination.

First group, Haptoglobin-administered group:

A 5% solution of haptoglobin in isotonic sodium chloride solution prepared according to the present invention was continuously administered drop-wise intravenously once a day at a dose of 0.8 g/kg (body weight).

Secod group, Hemoglobin-administered group:

A 10% solution of hemoglobin in isotonic sodium chloride solution isolated from red blood cells of the rabbit was continuously administered drop-wise intraveneously once a day at a dose of 0.4 g/kg (body weight).

Third group, Haptoglobin-hemoglobin-administered group:

Hemoglobin and then the haptoglobin of the invention were administered in the same manner and dose in the case of both the first and the second groups.

On the fourth day of administration, the survival of the rabbits of each group was examined. The results are shown in Table 9.

Table 9

| | Number of test | Number of survival | Number of dead |
|---|---|---|---|
| First group: Haptoglobin-administered | 10 | 10 | 0 |
| Second group: Hemoglobin-administered | 10 | 3 | 7 |
| Third group: Haptoglobin-hemoglobin-administered | 10 | 9 | 1 |

Histopathological comments on the test rabbits were as follows:

(1) First group:

Even in the case of a rabbit which had continuously been administered haptoglobin for 14 days, no change was observed in its kidney, spleen and lung, and only slight narrowing of sinusoid and deposition of iron were observed in the liver.

(2) Second group:

In the case of a rabbit which had continuously been administered hemoglobin for 6 days, marked deposition of iron was observed from proximal tuble to collecting tube of the kidney, thinning of renal epithelial cells was observed, propagation of reticular cells was observed in the spleen, and marked narrowing of sinusoid and deposition of iron were observed in the liver.

(3) Third group:

In the case of a rabbit which had continuously been administered hemoglobin and haptoglobin, deposition of iron was observed only in the proximal tuble of the kidney, the collecting tuble was substantially normal, no thinning of the epithelial cells was observed, slight infiltration of cells was observed in the spleen and less deposition of iron and much bile pigment were observed in the liver.

As is clear from the above-mentioned results, the haptoglobin obtained according to the present invention does not substantially bring about any adverse effects and has the excellent effect of preventing renal troubles caused by hemoglobin.

EXAMPLE 7

An example, in which the haptoglobin prepared in Example 2 was clinically applied to a patient, is illustrated below.

The patient was a male, 53 years old who had been severely stricken on the left waist with lumber that had fallen down during his work and had been sent to hospital as an emergency case. The diagnosis was pelvis fracture, urethra rupture and bleeding shock. Immediately after hospitalization, the patient was subjected to an operation for urinary tract reconstruction. During the operation, the total amount of bleeding was 7,500 ml, the total amount of blood transfused was 4,200 ml, and the total artificial expander transfused was 4,200 ml. Meanwhile, two ampules of Lasix ® (tradename for an injection manufactured by Japan Hoechst Co., each ampule had 2 ml of a solution containing 20 mg of furosemide) and 200 ml of 20% mannitol solution (manufactured by Daiichi Kagaku) were given, however, no improved effect was observed in the urine. The clinical progress of the patient after the operation is shown in the accompanying drawing. The symbol "↓" in the upper part of the drawing shows the time of addition of each chemical, and the symbol "↑" in the lower part of the drawing shows the time of operation and clinical findings. The abscissa shows days of progress after the accident. After 20 hours, the amount of urine was as small as 120 ml, and a significant amount of blood pigments were seen in the urine. At this stage, 250 ml of a 5% solution of the haptoglobin prepared according to the present invention in isotonic sodium chloride solution was administered to the patient drop-wise intravenously. As the result, the blood pigments disappeared from the urine within several hours after haptoglobin administration, and not only did the amount of urine increase but also the general symptoms of the patient were gradually improved. No adverse effect due to the administration of the haptoglobin preparation was observed even 6 months after the recovery of the patient.

age, having hypotensive substances as low as 10% or less, which can be safely administered in large amounts to a patient suffering from renal disorders derived from massive hemolysis.

Table 10

| Measured items | Experiment | 1 DEAE-cellulose | 2 DEAE-Sephadex | 3 TEAE-cellulose | 4 CM-cellulose | 5 CM-Sephadex | Example 1 QAE-Sephadex (reproduced) |
|---|---|---|---|---|---|---|---|
| Haptoglobin purity (%) | | 72 | 62 | 73 | 56 | 48 | 75 |
| Hemoglobin-binding capacity (mg hemoglobin/ mg haptoglobin) | | 0.60 | 0.59 | 0.58 | 0.61 | 0.62 | 0.62 |
| $LD_{50}$ (g/kg) | Mice | 11.7 or more | 11.7 or more | 11.7 or more | 11.7 or more | 11.7 or more | 11.7 or more |
| | Rats | 10.5 or more | 10.5 or more | 10.5 or more | 10.5 or more | 10.5 or more | 10.5 or more |
| Hypotensive activity (%) | | 18 | 21 | 12 | 9.8 | 9.0 | 9.5 |
| HB-Ag | | Negative | Negative | Negative | Negative | Negative | Negative |
| Stability at room temp. for 3 months | | Unchanged, clear | Changed Fine substances suspended | Unchanged, clear | Changed, Fine substances suspended | Changed, Fine substances suspended | Unchanged, clear |

EXAMPLE 8

Comparative experiments were carried out to select ion-exchangers suitable for the purification of human serum haptoglobin. The ion-exchangers employed in the experiments were QAE-Sephadex as a strongly basic ion-exchanger, DEAE-cellulose and DEAE-Sephadex as weakly basic ion-exchangers, TEAE-cellulose as a medium basic ion-exchanger, CM-cellulose and CM-Sephadex as weakly cationic ion-exchangers. The same method as in Example 1 was applied to these ion-exchangers used in place of QAE-Sephadex except that DEAE-cellulose (Experiment 1), DEAE-Sephadex (Experiment 2) and TEAE-cellulose (Experiment 3), in which haptoglobin was eluted by 0.12 M acetate buffer (pH 5.0) in Experiment 1, by 0.25 M acetate buffer (pH 5.0) in Experiment 2 and by 0.25 M acetate buffer (pH 5.0) in Experiment 3, respectively.

The results obtained are shown in Table 10.

The same method as in Example 1 was also applied except that the heat-treated solution was dialyzed against 0.05 M phosphate buffer solution (pH 7.0) in place of 0.05 M acetate buffer solution (pH 5.0) and then applied to CM-cellulose (Experiment 4) and CM-Sephadex (Experiment 5) in place of QAE-Sephadex, respectively, to adsorb impurities thereon, and a solution containing haptoglobin was separated as non-adsorbed fraction from the ion-exchangers, and was used as the "eluate" in the Example 1.

The results obtained are also included in Table 10.

It was concluded that it is necessary to use a strong basic ion-exchanger such as QAE-Sephadex or GE cellulose to obtain a haptoglobin solution stable in storage, having hypotensive substances as low as 10% or less, which can be safely administered in large amounts to a patient suffering from renal disorders derived from massive hemolysis.

What is claimed is:

1. A process for preparing a solution of human serum haptoglobin, characterized by subjecting an aqueous solution of α- and β-globulin fractions of human blood plasma to further fractionation by use of ammonium sulfate, collecting the fractions precipitated at an ammonium sulfate concentration between 30% W/V and 40% W/V saturation, contacting an aqueous reconstituted solution of the collected fractions with a strong anion exchanger which is epichlorhydrin-crosslinked diethyl (2-hydroxypropyl) aminoethyldextran or guanidoethyl cellulose to absorb haptoglobin onto said anion exchanger, eluting haptoglobin from the anion exchanger, concentrating the resulting eluate and forming the concentrated solution into a physiologically acceptable aqueous solution.

2. A process according to claim 1, comprising clarifying aqueous solution of α- and β-globulin fractions or the ammonium sulfate-precipitate by adding rivanol to the solution, separating the precipitates formed and then removing residual rivanol from the solution.

3. A process according to claim 1 comprising adding to the aqueous solution of haptoglobin at least one stabilizer selected from the group consisting of neutral amino acids, monosaccharides, disaccharides and soluble sugar alcohols, heating until the HB-Ag is inactivated and then freeing the solution from the stabilizer.

4. A process according to claim 1, wherein the strong anion exchanger is epichlorohydrin-crosslinked diethyl(2-hydroxypropyl)aminoethyldextran.

5. A process according to claim 1, wherein the aqueous eluate is concentrated by precipitating with ammonium sulfate precipitation method.

6. A process according to claim 1, wherein the aqueous eluate is concentrated by dialysis under reduced pressure.

7. A process according to claim 1, wherein the physiologically acceptable aqueous solution is in the form of an isotonic sodium chloride solution.

8. A process according to claim 2, wherein the residual rivanol is removed by dialysis against buffer solution.

9. A process according to claim 2, wherein the residual rivanol is removed by adsorption on bentonite, terra alba or active carbon.

10. A process according to claim 3, wherein the stabilizing agent is a neutral amino acid and is glycine, alanine, valine, leucine or isoleucine.

11. A process according to claim 3, wherein the stabilizing agent is a monosaccharide and is glucose, mannose, galactose or fructose.

12. A process according to claim 3, wherein the stabilizing agent is a disaccharide and is sucrose, maltose or lactose.

13. A process according to claim 3, wherein the stabilizing agent is a soluble sugar alcohol and is mannitol, sorbitol or xylitol.

14. A process according to claim 3, wherein the aqueous solution of haptoglobin is heated at 60° C. for 10 hours.

15. A process according to claim 3, wherein the stabilizer is removed by dialysis.

16. A process according to claim 3, wherein the amount of the stabilizer added is at least 5% by weight based on the volume of the solution.

17. A process according to claim 3, wherein the amount of the stabilizer added is 15 to 20% by weight based on the volume of the solution.

* * * * *